(12) United States Patent
Timms et al.

(10) Patent No.: US 6,960,668 B2
(45) Date of Patent: Nov. 1, 2005

(54) PROCESS FOR THE PRODUCTION OF SUBSTITUTED THIOXANTHONES

(75) Inventors: Allan William Timms, Cheshire (GB); William Arthur Green, Cheshire (GB)

(73) Assignee: Great Lakes (UK) Limited, Chesire (GB)

( * ) Notice: Subject to any disclaimer, the term of this patent is extended or adjusted under 35 U.S.C. 154(b) by 102 days.

(21) Appl. No.: 10/613,303

(22) Filed: Jul. 3, 2003

(65) Prior Publication Data

US 2004/0059133 A1 Mar. 25, 2004

(30) Foreign Application Priority Data

Jul. 13, 2002 (GB) .............................. 0216311

(51) Int. Cl.⁷ ........................................ C07D 335/08
(52) U.S. Cl. ...................................... 549/27
(58) Field of Search ......................... 549/27

(56) References Cited

U.S. PATENT DOCUMENTS

| | | | |
|---|---|---|---|
| 4,103,015 A | | 7/1978 | Hodson et al. |
| 4,385,182 A | | 5/1983 | Fischer et al. |
| 4,418,138 A | * | 11/1983 | Curtis ................... 430/253 |
| 4,450,279 A | * | 5/1984 | Shirosaki et al. ........... 549/27 |
| 4,505,794 A | | 3/1985 | Kvita et al. |
| 4,661,595 A | | 4/1987 | Avar |

FOREIGN PATENT DOCUMENTS

| | | |
|---|---|---|
| EP | 0 520 574 | 12/1992 |
| EP | 1 211 252 | 6/2002 |
| GB | 1 447 032 | 8/1976 |
| WO | PCT-WO 98/42697 | 10/1998 |

OTHER PUBLICATIONS

European Search Report dated Sep. 12, 2003 received Mar. 29, 2004 for European Patent Application No. EP 03 25 4067.
Annex to the European Search Report dated Sep. 12, 2003 and received Mar. 29, 2004 for European Patent Application No. EP 03 25 4067.
Database Crossfire Beilstein 'Online! Beilstein Institut zur Förderung der Chemischen Wissenschaften, Frankfurt am Main, DE; XP002254438.
Database Crossfire Beilstein 'Online! Beilstein Institut zur Förderung der Chemischen Wissenschaften, Frankfurt am Main, DE; XP002254439.
Database Crossfire Beilstein 'Online! Beilstein Institut zur Förderung der Chemischen Wissenschaften, Frankfurt am Main, DE; XP002254440.
Database Crossfire Beilstein 'Online! Beilstein Institut zur Förderung der Chemischen Wissenschaften, Frankfurt am Main, DE; XP002254441.
Database Crossfire Beilstein 'Online! Beilstein Institut zur Förderung der Chemischen Wissenschaften, Frankfurt am Main, DE; XP002254442.
Database Crossfire Beilstein 'Online! Beilstein Institut zur Förderung der Chemischen Wissenschaften, Frankfurt am Main, DE; XP002254443.
Davis et al., "New Synthesis of Thioxanthone and its Derivatives," J. Chem. Soc., vol. 97, 1910, pp. 1290–1299, XP009017242.
Lougnot et al., "Water–Soluble Polymerization Initiators Based on the Thioxanthone Structure," Macromolecules, vol. 22, 1989, pp. 108–116, XP001154961.
Pouliquen et al., "Functionalized Polysiloxanes with Thioxanthone Side Groups: A Study of Their Reactivity as Radical Polymerization Macroinitiators," Macromolecules, American Chemical Society. vol. 28, No. 24, Nov. 20, 1995, pp. 8028–8034, XP000539427.
Database Crossfire Beilstein 'Online! Beilstein Institut zur Förderung der Chemischen Wissenschaften, Frankfurt am Main, DE; XP002254444.
Houben–Weyl, Methoden der organischen Chemie, Band E4: "Kohlensäure–Derivate," Thieme Verlag, Stuttgart, 1983, 64–65, XP002254436.
Houben–Weyl, Methoden der organischen Chemie, Band VIII: "Sauerstoffverbindungen III," Thieme Verlag, Stuttgart, 1952, 105, XP002254437.

* cited by examiner

Primary Examiner—Deborah C. Lambkin
(74) Attorney, Agent, or Firm—Marshall Gerstein & Borun LLP

(57) ABSTRACT

A one-step process for the preparation of a substituted thioxanthone, such as carboxymethoxythioxanthone, in high yields and as a single isomer. The substituted aryl compound is reacted with mercaptobenzoic acid or dithiobisbenzoic acid in the presence of sulphuric acid.

12 Claims, No Drawings

PROCESS FOR THE PRODUCTION OF SUBSTITUTED THIOXANTHONES

The present invention relates to an improved process for the production of substituted thioxanthones.

Various routes for the synthesis of substituted thioxanthones have been described. See, for example, J. Chem. Soc. 1910 (97), 1297, Davis and Smiles; J. Chem. Soc. 1911 (99), 1355, Marsden and Smiles; J. Indian Chem. Soc. 1929 (6), 273, Sen and Sen-Gupta and WO97/49664, Anderson et al. Lambson Fine Chemicals Ltd.

Whilst conventional synthetic routes to substituted thioxanthones are adequate, they do have a number of drawbacks. The routes can result in low yields of the desired product and/or mixtures of isomers and by-products that may be difficult to separate or purify. Thioxanthones with side chains containing a chemically reactive group are conventionally made by further synthetic steps from the thioxanthone molecule and can involve two, three or four stages, resulting in the production of such molecules being a time consuming and inefficient process with low overall yields.

An example of a conventional synthetic route to 2-carboxymethoxythioxanthone involves three stages. Firstly, phenol is reacted with dithiobisbenzoic acid to produce 2-hydroxythioxanthone in a 60% yield. Secondly, the 2-hydroxythioxanthone is reacted with ethyl bromoacetate to produce the ethyl ester of 2-carboxymethoxythioxanthone in 75% yield. Thirdly, the ester is hydrolysed by acidification to produce the desired product in 90% yield. These three stages form an inefficient and time-consuming process to provide a product that is a dark colour, contains impurities and by-products and is produced with only an overall yield of 40% from the starting material.

Substituted thioxanthones with side chains containing reactive groups are important intermediates in the pharmaceutical and photochemical industries. Therefore, an improved process for producing these intermediates in higher yields, with fewer steps and with less impurities would be desirable.

It is object of the present invention to provide an improved process for the production of thioxanthone derivatives containing side chains with chemically reactive side groups that aims to overcome, or at least alleviate, the above-mentioned drawbacks.

Accordingly, the present invention provides a process for the production of thioxanthone derivatives of the general formula (I) given below:

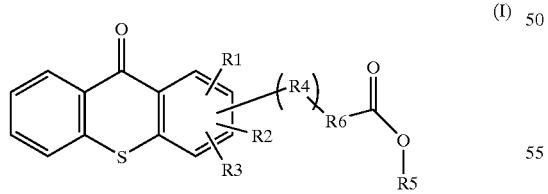

where:
$R_1$, $R_2$ and $R_3$ is hydrogen, $C_1$–$C_{10}$ alkyl, $C_1$–$C_{10}$ alkoxy, halogen, hydroxy or $C_1$–$C_2$ dialkylamino; $R_1$, $R_2$ and $R_3$ being the same or different;
R4 is oxygen, sulphur or absent;
$R_5$ is hydrogen, $C_1$–$C_{10}$ alkyl or aryl; and
$R_6$ is a straight or branched alkyl chain having 0 to 10 carbon atoms;

the one-step process comprising reacting a compound of given general formula (II) below with mercaptobenzoic acid or dithiobisbenzoic acid in the presence of sulphuric acid:

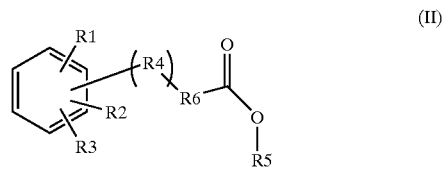

Preferably $R_6$ is —$(CH_2)_n$— where n is 0 to 10 or —$CH(CH_3)$—.

Preferably, the compound of formula (II) is phenoxyacetic acid, where $R_1$, $R_2$, $R_3$ and $R_5$ are each hydrogen, $R_4$ is oxygen and n=1, thereby producing 2-carboxymethoxythioxanthone.

Preferably, the sulphuric acid is used in amounts of 1 part to about 20 parts by weight of acid to 1 part by weight of dithiobisbenzoic or mercaptobenzoic acid. The concentration of the acid is preferably greater than or equal to 90%.

The molar ratios of dithiobisbenzoic acid or mercaptobenzoic acid to a compound of formula (II) may vary between about 1:1 to 1:5.

Preferably, the reactants are stirred for a sufficient time to complete the reaction. The reaction temperature during the addition of the reactants is preferably in the range 0° C. to 30° C. but may be increased during the reaction from about 30° C. to about 90° C. The reaction time is preferably 0.5 to 6 hours.

The product is preferably isolated from the reaction mixture by quenching with excess water and filtering the solid product. Preferably, water is added to dilute the acid strength to about 20 to 50%. The filtered product may be washed with water. The product may be further purified, if required, by means of crystallisation or slurry in an appropriate solvent.

The resultant thioxanthone compound is substantially free of impurities and may be provided in yields of up to 80%. Additionally, a single isomer is obtained.

The present invention further comprehends novel thioxanthone compounds as follows:

1,2-Dimethyl-4-carboxymethoxythioxanthone,

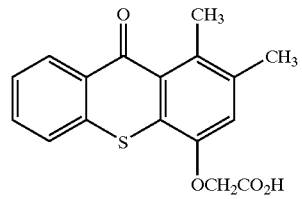

1-Chloro-4-carboxymethoxythioxanthone,

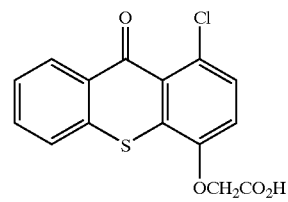

-continued
1-Carboxymethoxy-4-methoxythioxanthone,

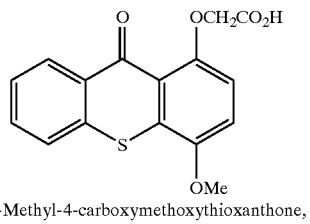

1-Methyl-4-carboxymethoxythioxanthone,

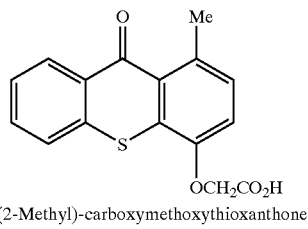

2-(2-Methyl)-carboxymethoxythioxanthone,

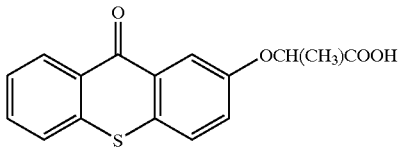

The present invention will now be further illustrated by means of the following Examples in which Example 1 describes the synthesis of 2-carboxymethoxythioxanthone from dithiobisbenzoic acid according to the method of the present invention and Example 2 describes the synthesis of 2-carboxymethoxythioxanthone from mercaptobenzoic acid according to the method of the present invention.

EXAMPLE 1

Preparation of 2-carboxymethoxythioxanthone from dithiobisbenzoic acid. Concentrated sulphuric acid (500 g) and dithiobisbenzoic acid (30.6 g) were charged to a reactor and phenoxyacetic acid (60.8 g) was added over 1 hour keeping the temperature at 0–25° C. After stirring for 1 hour, water (470 mls) was added. The solid product was filtered and washed with water (2×50 mls). The solid was then stirred in 50% aqueous acetone (200 mls) and heated to reflux for 0.5 hours. After cooling to ambient temperature the solid was filtered, washed with water and dried. 2-Carboxymethoxythioxanthone (43.4 g) was obtained in 76% yield. This was a dull yellow solid, melting point 207–212° C. Assay by HPLC>97%. A single isomer was obtained.

EXAMPLE 2

Preparation of 2-carboxymethoxythioxanthone from mercaptobenzoic acid. Concentrated sulphuric acid (250 g) and mercaptobenzoic acid (15.4 g) were charged to a reactor and phenoxyacetic acid (25.8 g) was added over 1 hour keeping the temperature at 5–25° C. The temperature was raised to 50–60° C. for 1 hour then water (270 mls) was added. The solid product was filtered and washed with water (2×50 mls). The solid was stirred in 120 mls 50% aqueous acetone and brought to reflux for 0.5 hours. After cooling to 15° C., the solid was filtered, washed with water and dried. 2-Carboxymethoxythioxanthone (13.5 g) was obtained in 47% yield. This was pale yellow solid, melting point 210–215° C. Again, a single isomer of the product was produced.

The present invention enables a substituted thioxanthone compound to be provided that is substantially free of impurities and can be isolated in yields of up to, and possibly in excess of, 80% and as a single isomer.

This invention displays a yield from a single stage process that greatly exceeds that from alternative multi-stage conventional synthetic routes and provides material which is essentially free of impurities. The thioxanthone compounds so produced are useful as reactive intermediates in the pharmaceutical and photochemical industries.

EXAMPLE 3

Preparation of 1,2-dimethyl-4-carboxymethoxythioxanthone

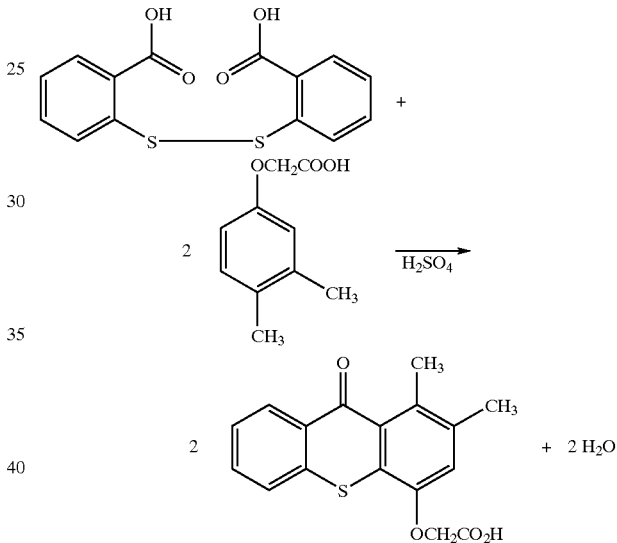

Concentrated sulphuric acid (115 cm$^3$) and dithiobisbenzoic acid (12.2 g) were charged to a reactor and 3,4-dimethylphenoxyacetic acid (25.2 g) was added over 1 to 2 hours at 10° to 15° C. with cooling. After stirring for a further 1 hour at 10° to 20° C., then at 30° to 40° C. for 2 hours a bright red solution was obtained. This reaction mixture was then quenched onto water (230 mls) whilst allowing the temperature to rise to ~80° C. The quenched mixture was stirred for a further 25 minutes at ~80° C. then cooled to 30° C. The resulting precipitate was filtered, washed with water and dried.

The resulting crude product was slurried in a mixture of water (80 mls), acetic acid (25 mls), and 2-butanone (45 mls) at reflux for 30 minutes, cooled to ambient temperature and filtered. The damp product cake was washed with a mixture of water and 2-butanone followed by water, then dried. 1,2-Dimethyl-4-carboxymethoxythioxanthone (13.7 g) was obtained in 54.4% yield. This was a bright yellow solid, melting point 226° to 229° C. Assay by hplc>98%.

EXAMPLE 4

Preparation of 1-chloro-4-carboxymethoxythioxanthone

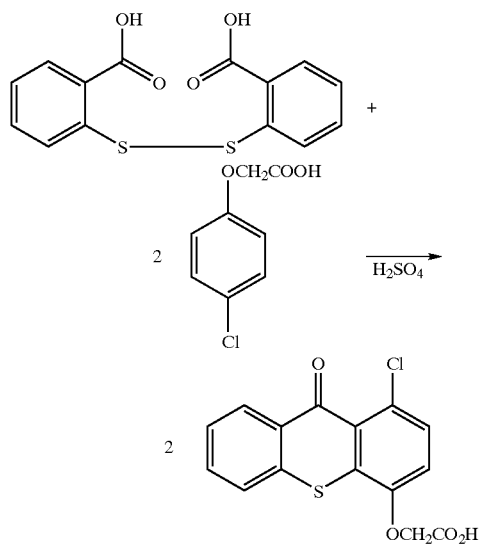

Concentrated sulphuric acid (120 mls) and dithiobisbenzoic acid (12.2 g) were charged to a reactor and 4-chlorophenoxyacetic acid (26.1 g) was added over 1 to 2 hours at 10° to 15° C. with cooling. After stirring for a further 1 hour at 10° to 20° C., then at 30° to 40° C. for 2 hours a deep red solution was obtained. This reaction mixture was then quenched onto water (250 mls) whilst allowing the temperature to rise to ~80° C. The quenched mixture was stirred for a further 25 minutes at ~80° C. then cooled to 30° C. The resulting precipitate was filtered, washed with water and dried.

The resulting crude product was slurried in a mixture of water (80 mls), acetic acid (25 mls), and 2-butanone (45 mls) at reflux for 30 minutes, cooled to ambient temperature and filtered. The damp product cake was washed with a mixture of water and 2-butanone followed by water, then dried. 1-Chloro-4-carboxymethoxythioxanthone (18.9 g) was obtained in 73.8% yield. This was a pale dull yellow solid, melting point 230° to 232° C.

EXAMPLE 5

Preparation of 1-carboxymethoxy-4-methoxythioxanthone

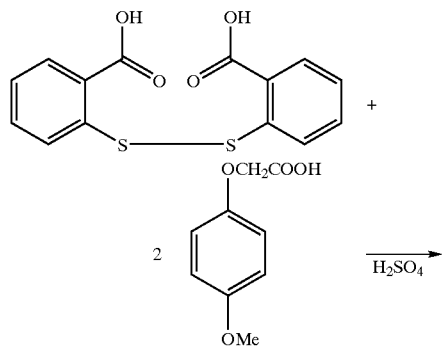

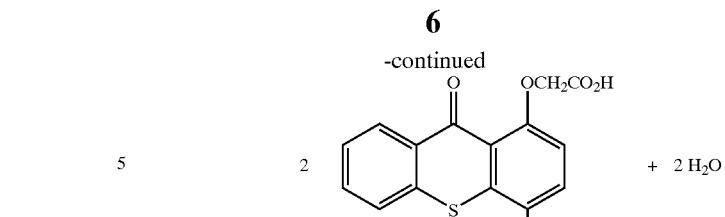

Concentrated sulphuric acid (120 mls) and dithiobisbenzoic acid (12.2 g) were charged to a reactor and 4-methoxyphenoxyacetic acid (25.5 g) was added over 1 to 2 hours at 10° to 15° C. with cooling. After stirring for a further 1 hour at 10° to 20° C., then at 30° to 40° C. for 2 hours a deep red solution was obtained. This reaction mixture was then quenched onto water (250 mls) whilst allowing the temperature to rise to ~80° C. The quenched mixture was stirred for a further 25 minutes at ~80° C. then cooled to 40° C. The resulting precipitate was filtered and then washed with water.

The resulting crude product was slurried in a mixture of water (80 mls), acetic acid (25 mls), and 2-butanone (45 mls) at reflux for 30 minutes, cooled to ambient temperature and filtered. The damp product cake was washed with a mixture of water and 2-butanone followed by water, then dried. 1-Carboxymethoxy-4-methoxythioxanthone (16.8 g) was obtained in 66.4% yield. This was an orange/yellow powder, melting point 223° to 225° C.

EXAMPLE 6

Preparation of 1-methyl-4-carboxymethoxythioxanthone

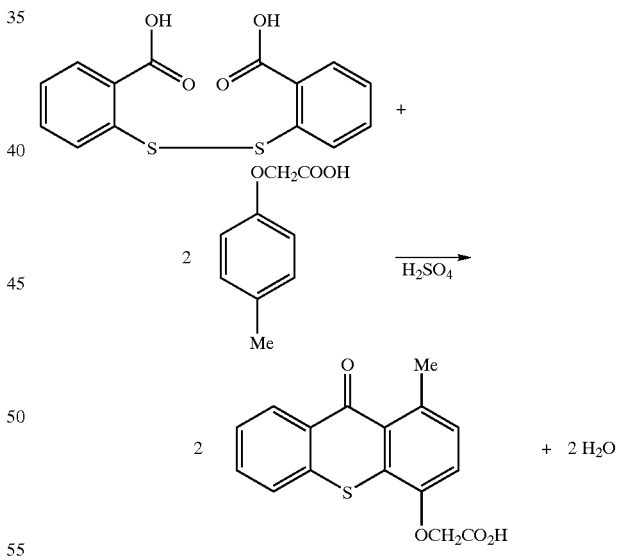

Concentrated sulphuric acid (120 mls) and dithiobisbenzoic acid (12.2 g) were charged to a reactor and 4-methylphenoxyacetic acid (19.9 g) was added over 1 to 2 hours at 10° to 15° C. with cooling. After stirring for a further 1 hour at 10° to 20° C., then at 30° to 40° C. for 2 hours a deep red solution was obtained. This reaction mixture was then quenched onto water (250 mls) whilst allowing the temperature to rise to ~80° C. The quenched mixture was stirred for a further 25 minutes at ~80° C. then cooled to 30° C. The resulting precipitate was filtered and then washed with water and dried.

The resulting crude product was slurried in a mixture of water (60 mls), acetic acid (20 mls), and 2-butanone (30 mls) at reflux for 30 minutes, cooled to ambient temperature and filtered. The damp product cake was washed with a mixture of water and 2-butanone followed by water, then dried. 1-Methyl-4-carboxymethoxythioxanthone (14.0 g) was obtained in 58.3% yield. This was a pale yellow powder, melting point 198° to 235° C.

EXAMPLE 7

Preparation of 2-(2-methyl)-carboxymethoxythioxanthone

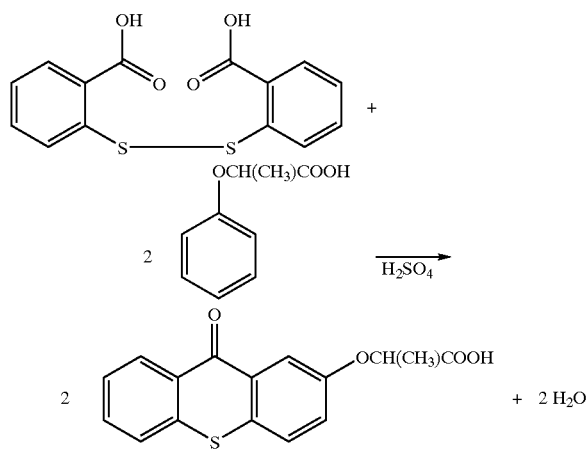

Concentrated sulphuric acid (120 mls) and dithiobisbenzoic acid (12.2 g) were charged to a reactor and 2-phenoxypropionic acid (23.3 g) was added over 1 to 2 hours at 10° to 15° C. with cooling. After stirring for a further 1 hour at 10° to 20° C., then at 30° to 40° C. for 2 hours a deep red solution was obtained. This reaction mixture was then quenched onto water (250 mls) whilst allowing the temperature to rise to ~80° C. The quenched mixture was stirred for a further 25 minutes at ~80° C. then cooled to 30° C. The product precipitated as an oily mass which was slurried in a mixture of water (80 mls), acetic acid (30 mls), and 2-butanone (40 mls) at reflux for 30 minutes, cooled to ambient temperature and filtered. The damp product cake was washed with a mixture of water and 2-butanone followed by water, then dried.

2-(2-Methyl)-carboxymethoxythioxanthone (13.6 g) was obtained in 56.37% yield. This was a green powder, melting point=174° to 177° C.

What is claimed is:

1. A process for the production of thioxanthone derivatives of the general formula (I) given below:

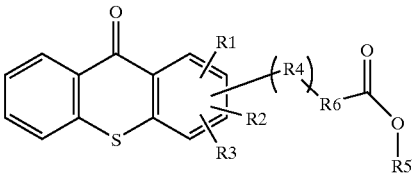

where:
$R_1$, $R_2$ and $R_3$ is hydrogen, $C_1$–$C_{10}$ alkyl, $C_1$–$C_{10}$ alkoxy, halogen, hydroxy or $C_1$–$C_2$ dialkylamino; $R_1$, $R_2$ and $R_3$ being the same or different;
$R_4$ is oxygen, sulphur or absent;
$R_5$ is hydrogen, $C_1$–$C_{10}$ alkyl or aryl; and
$R_6$ is a straight or branched alkyl chain having 0 to 10 carbon atoms;
the one-step process comprising reacting a compound of the general formula (II) below with mercaptobenzoic acid or dithiobisbenzoic acid in the presence of sulphuric acid:

(II)

2. A process as claimed in claim 1, wherein $R_6$ is —$(CH_2)_n$—, n being 0 to 10.
3. A process as claimed in claim 1, wherein the compound of formula (II) is phenoxyacetic acid where $R_1$, $R_2$ $R_3$ and $R_5$ are each hydrogen, $R_4$ is oxygen and n is 1.
4. A process as claimed in claim 1, wherein $R_6$ is —$CH(CH_3)$—.
5. A process as claimed in any one of claims 1 to 4, wherein the sulphuric acid is used in amounts 1 part to 20 parts by weight of acid to 1 part by weight of dithiobisbenzoic acid or mercaptobenzoic acid.
6. A process as claimed in claim 1, wherein the sulphuric acid has a concentration of equal to or greater than 90%.
7. A process as claimed in claim 1, wherein the molar ratios of dithiobisbenzoic acid or mercaptobenzoic acid to a compound of formula (II) are 1:1 to 1:5.
8. A process as claimed in claim 1 further comprising stirring the reactants to aid completion of the reaction.
9. A process as claimed in claim 1, wherein the temperature of the reaction is kept at 0° C. to 30° C. during addition of the reactants.
10. A process as claimed in claim 9, wherein the temperature is increased to 30° C. to 90° C. following addition of the reactants.
11. A process as claimed in claim 1 further comprising quenching the reactant mixture with excess water and filtering the solid product.
12. A process as claimed in claim 9, wherein water is added to dilute the acid strength to 20–50%.

* * * * *